United States Patent [19]

Stjernschantz et al.

[11] Patent Number: 5,760,075
[45] Date of Patent: Jun. 2, 1998

[54] METHOD AND MEANS FOR PREVENTION AND TREATMENT OF SECONDARY CATARACT

[75] Inventors: Johan Stjernschantz; Bahram Resul, both of Upsala, Sweden

[73] Assignee: Pharmacia & Upjohn AB, Stockholm, Sweden

[21] Appl. No.: 809,343

[22] PCT Filed: Sep. 19, 1995

[86] PCT No.: PCT/SE95/01058

§ 371 Date: May 12, 1997

§ 102(e) Date: May 12, 1997

[87] PCT Pub. No.: WO96/09054

PCT Pub. Date: Mar. 28, 1996

[30] Foreign Application Priority Data

Sep. 21, 1994 [SE] Sweden .................... 9403160

[51] Int. Cl.$^6$ .................... A61K 31/215; A61K 31/19
[52] U.S. Cl. .................... 514/530; 514/573; 514/912
[58] Field of Search .................... 514/530, 573, 514/912

[56] References Cited

FOREIGN PATENT DOCUMENTS 0242580  10/1987  European Pat. Off. .
0453127  10/1991  European Pat. Off. .

Primary Examiner—Zohreh Fay
Attorney, Agent, or Firm—Dinsmore & Shohl LLP

[57] ABSTRACT

The present invention relates to a method for treatment or prevention of secondary cataract, comprising contacting the surface of the eye with an effective amount of a therapeutically active and physiologically acceptable prostaglandin comprising a prostaglandin A, a prostaglandin J, a derivative of prostaglandin A or a derivative of prostaglandin J.

20 Claims, No Drawings

METHOD AND MEANS FOR PREVENTION AND TREATMENT OF SECONDARY CATARACT

Secondary cataract is a condition characterized by opacification of the posterior lens capsule after cataract surgery. The opacification usually becomes manifest 2–10 years after surgery, but the formation of secondary cataract in young children may be much quicker. When the lens with age or due to different pathological conditions becomes opaque cataract ensues. There are many kinds of cataract depending on the cause of the opacification. So far cataract can only be treated surgically by removing the lens. The cataractous lens can be removed with the capsule in its entirety which is called intracapsular cataract extraction. Presently, however, a more common procedure is to remove the lens with part of its anterior capsule only, thus leaving the posterior lens capsule in the eye intact. This procedure is called extracapsular cataract extraction. In such eyes usually an intraocular artificial lens is implanted into the remaining lens capsule bag and in most cases good vision is restored.

A problem, however, is that in the extracapsular cataract extraction technique with implantation of an artificial lens into the eye, remnants of the lens, its epithelium, and possibly also other cells are commonly not completely removed. Frequently these tissue remnants slowly starts to proliferate and with time tend to opacify the posterior lens capsule so that vision is impaired. This condition is, as mentioned above, called secondary cataract. After ordinary uneventful extracapsular cataract surgery secondary cataract develops to a point when it interferes with functional vision, usually within 2–10 years, but it may be faster and in some cases may not develop at all.

A number of different ways to prevent secondary cataract have been suggested over the years, both with regard to the intraocular lens as such and the technique used in surgery. So has for instance Hoffer in U.S. Pat. No. 4,244,060 described a lens that has a barrier ridge on the side facing the capsule wall. The intention was to create a mechanical barrier inhibiting migration of residual lens epithelial cells and their derivatives into the optical zone behind the IOL.

Administration of various types of drugs during surgery for preventing opacification is another approach that has been found to be of potential importance. Examples of such drugs are colchicine and 5-fluorouracil.

Colchicine is a mitosis-inhibiting phenanthrene derivative isolated from *Colchicum autumnale*. Colchicine arrests mitosis at metaphase by binding to a protein present in microtubules, hence interfering with the structure of the mitotic spindle. The substance has been shown to be a potent inhibitor of lens epithelial cell proliferation and migration. However, colchicine has a low therapeutic index with a lot of potential side effects, including a temporary toxic effect on the optic nerve when used for preventing posterior capsule opacification in primates.

5-Fluorouracil is a potent anti mitotic drug affecting the DNA replication and is widely used in the treatment of epithelial tumours. Ruitz et al (Inhibition of posterior capsule opacification by 5-fluorouracil in rabbit; Ophthalmic Res. 22 (1990) 201–208) have also shown that this substance reduces posterior capsule opacification in vivo in rabbits.

Even if there are reports claiming the potential use of drugs of the type mentioned above, currently the only reasonably successful way to clinically treat secondary cataract is by performing a capsulatomy. This can be done surgically but is usually carried out by a YAG-laser. Generally the result of such YAG-laser capsulotomy is good and in most cases good functional vision is restored. However, a problem with this procedure is that complications in the posterior segment of the eye may ensue. Such complications comprise e.g. macular edema. It seems reasonable to believe that also in cases of very qualified surgery there might be some remnant cells in the capsular bag forming a potential basis for cell attachment and growth in the optic area of the posterior capsule, even if delayed to some extent. Therefor it would be desirable to prevent or treat secondary cataract medically by using drugs that are applied topically on the eye, and not only in one single administration in connection with surgery.

We have now unexpectedly found that certain prostaglandins may be useful for preventing secondary cataract or for treating secondary cataract when already manifest.

Prostaglandins are fatty acids usually derived from the precursors eicosatrienoic, eicosatetraenoic or eicosapentanoic acid through metabolic steps involving oxygenation. The prostaglandins typically carry a cyclopentane ring to which two carbon chains link, the upper usually being called the alpha chain and the lower usually being called the omega chain. Naturally occurring prostaglandins have the general structure:

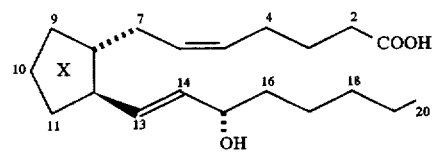

in which the cyclopentyl ring X is

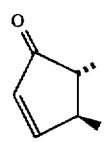

A

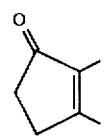

B

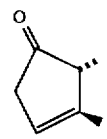

C

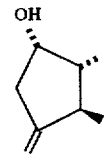

D

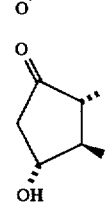

E

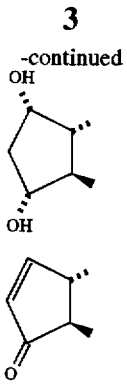

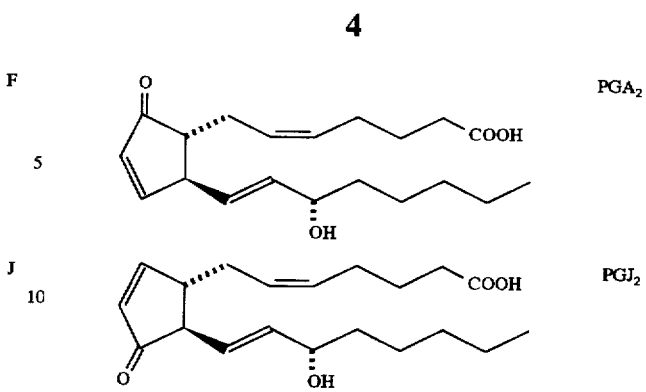

Depending on the number of double bonds in these chains subscripts of 1 to 3 are given. In prostaglandins with subscript 1, e.g. $PGA_1$ and $PGJ_1$, the double bond is situated between carbons 13 and 14 in the omega chain, and it exhibits trans configuration in naturally occurring prostaglandins. In prostaglandins with subscript 2, e.g. $PGA_2$ and $PGJ_2$ an additional double bond in the cis configuration exists between carbon 5 and 6 in the alpha chain and finally in prostaglandins with subscript 3 an additional third double bond is situated between carbons 17 and 18 in the omega chain. In naturally occurring this double bond exhibits cis configuration. The hydroxyl group on carbon 15 carried by natural prostaglandins seems to be essential for biologic activity.

Prostaglandins and typically $PGF_{2\alpha}$ and its derivatives, especially the esters, reduce the intraocular pressure (IOP) and the use of prostaglandins and their derivatives as IOP lowering agents is described in several patents and patent applications, see for instance U.S. Pat. No. 4,599,353 (Bito), U.S. Pat. No. 4,952,581 (Bito), WO89/03384 (Resul and Stjernschantz), EP 170258 (Cooper), EP 253094 (Goh) and EP 308135 (Ueno).

Prostaglandins of A and J type and their analogues and derivatives have been found important for treatment of cataract, e.g. opacification of the natural crystalline lens. This is however a quite different condition compared to the now claimed application. Their importance for treatment of cataract is believed to be related to the existence of an alpha beta unsaturated ketone in the cyclopentane ring. The alpha beta unsaturated ketone is very reactive forming adducts with thiol groups, such as e.g. sulfhydryl groups on proteins. Accordingly, prostaglandins exhibiting such thiol-binding groups reacts with the crystallins of the lens to form thiol adducts thereby preventing the sulfhydryl groups from producing disulfide bridges between lens proteins, and thus preventing the proteins from aggregating upon oxidative stress. The use of PGA and PGJ type prostaglandins for treatment of cataract is the subject of a pending patent application SE 9303627-5. It does not need to be pointed out, as obvious from the description given above, that cataract and secondary cataract are two different indications and that the fact that opacification of the natural lens can be prevented by certain prostaglandins doesn't make the cell inhibitory effect utilized in secondary cataract obvious.

For use according to the present invention compounds with an $\alpha,\beta$-unsaturated cyclopentenone structure and esp. prostaglandins of type A and J seem to be of special importance and among these in particular $PGA_2$ and $PGJ_2$ as well as their analogues and derivatives. $PGA_2$ is probably not a naturally occurring compound in man, but is formed from $PGE_2$ during acid extraction. $PGJ_2$ on the other hand is a well known metabolite of $PGD_2$, which is a naturally occurring prostaglandin. The molecular structures of $PGA_2$ and $PGJ_2$ are depicted below:

EXEMPLIFICATION OF THE INVENTION

The invention is exemplified with the following non-limiting examples. Prostaglandin A2 ((5Z, 13E, 15S)-15-hydroxy-9-oxoprosta-5,10,13-trien-1-oic acid) and prostaglandin J2 ((5Z,13E,15S)-15-hydroxy-11-oxoprosta-5,9,13-trien-1-oic acid) were purchased from Cayman Chemical Company (Ann Arbor, Mich., USA) and used in acid form. Both compounds were dissolved in ethanol, and diluted to the final concentrations in the cell growth medium. Lens epithelial cell cultures were established from explants of New Zeeland albino rabbit lenses. For the experiments, cells were cultured in equal parts of Dulbecco's modified Eagle medium and Ham's F-12 supplemented with 5% fetal calf serum and 50 µg/ml gentamycin at 37° C. in 5% $CO_2$, humidified air. The effects of the prostaglandins on cells at passage 4 were examined with a photometric cell proliferation assay after 8 days of continuous exposure. Cells were seeded into multiwell tissue culture plates containing culture medium and quadruplicates of 5 nanomolar to 50 micromolar of the test compounds. Culture medium only, served as control. Every second day, the culture medium was exchanged with fresh medium including the appropriate concentration of fresh prostaglandin to provide the cells with sufficient nutrients and to avoid problems that could arise from degradation of the test compound in the culture medium. After 8 days, the cells were fixed in glutaraldehyde (1%), stained by crystal violet (0.1%) and the stain was eluted by Na-lauryl sulphate (2.5%). The absorbance of the colored solutions, shown to be linearly related to cell number, was monitored photometrically. Results were expressed as relative growth e.g. absorbance of treated versus untreated cultures. The experiment was repeated once in its entirety and was performed blindly, i.e. the examiner did not know the name or the nature of the compounds.

The tests clearly demonstrated that both $PGA_2$ and $PGJ_2$ markedly inhibited cell growth and reduced the total number of cells (see FIGS. 1 and 2). The highest concentration, 50 micromolar, of both $PGA_2$ (compound 1) and $PGJ_2$ (compound 3); reduced the total number of cells to less than 25% of the original cell number and the half maximal response of the reduction was obtained at around 10 micromolar concentration. The vehicle (compound no 2) which served as control had no effect. Thus both $PGA_2$ and $PGJ_2$ had marked inhibitory effect on the cultured rabbit lens epithelial cells.

From these experiments carried out in a relevant in vitro model it is obvious that prostaglandins of the A and J type are potentially very useful clinically for prevention or treatment of secondary cataract. Since these prostaglandins not only halt the growth of lens epithelial cells but in addition seem to exterminate these cells it is furthermore possible that already manifest secondary cataract can be cured. In the exemplification given above only two prostaglandins, namely $PGA_2$ and $PGJ_2$ were used but it is obvious that also analogues and derivatives of prostaglandins of type A and J with the same fundamental mechanism of action may also be employed. Such derivatives include, but is not limited to, compounds containing alkyl substituents, esp. lower alkyl groups with 1–5 carbon atoms, halogen atoms, etc. in the alpha chain, the omega chain or the pentyl ring. An essential characteristic of such substituents is that they don't considerably decrease the cell growth inhibiting effect or negatively influence the ophthalmic usefulness of the compound. Analogues of PGA are e.g. 16,16-dimethyl-PGA$_1$, $\Delta^7$-PGA$_1$, $\Delta^7$-PGA$_2$ and 16,16-dimethyl-PGA$_2$. Analogues of PGJ are e.g. $\Delta^{12}$-PGJ$_2$ and various esters thereof.

A particular problem in the eye is the delivery of the drug to the site of action, since the corneal epithelium is an effective barrier, preventing transcorneal diffusion of even relatively small hydrophilic molecules. Thus PGA and PGJ or their analogues or derivatives as discussed above may be modified to more lipophilic substances by esterification of different parts of the molecule, e.g. the carboxylic acid moiety. The group of esters to be used clinically comprises alkyl esters with up to 10 carbon atoms, esp. lower alkyl esters e.g. methyl, ethyl, and isopropyl or cyclic esters such as benzyl. Also other lipophilic derivatives like amides can be employed.

The prostaglandin compounds, including acid forms, esters and amides, should be used in a suitable vehicle for topical application on the eye. The group of suitable vehicles include aqueous solutions with or without solubilizers, stabilizer such as cyclodextrins, oils, ointments, micellar systems, nanoparticles and various slow release formulations such as ocular soluble or insoluble inserts. Such vehicles may optionally contain preservatives depending on whether they are intended for single or multiple use. Various preservatives that may be employed comprise e.g. benzalkonium chloride, chlorhexidine, thiomersal, parabenzoic acid and other compounds with satisfactory antimicrobial effect.

The method of the invention for prevention or treatment of secondary cataract comprises topical administration after cataract extraction of a formulation containing an ophthalmologically acceptable PGA or PGJ derivative that effectively inhibits the growth of lens epithelial cells and other cells. The derivative is topically applied once or several times daily either prophylactically to prevent the formation of secondary cataract or to treat secondary cataract that is already manifest. Such treatment may take only a few months or may go on chronically and even life-long treatment may be employed depending on the clinical situation. The recommended dose to be used depends on the particular prostaglandin and its physical-chemical characteristics but is usually in the range from 0.01–100 microgram per application, preferably in a dose of 1–50 microgram per application. The medication can be administered once or several times daily, depending on the clinical situation, and the dose form. When the secondary cataract has regressed so that the patient's vision is restored treatment may continue intermittently or may be terminated.

The invention is also related to the use of a prostaglandin derivative or analogue of the A or J type, as discussed above, for preparation of an ophthalmological composition for treatment of secondary cataract, as well as to the composition as such, especially compositions adapted for ophthalmological use.

We claim:

1. A method for treatment or prevention of secondary cataract, comprising contacting the surface of the eye with an effective amount of a therapeutically active and physiologically acceptable prostaglandin comprising a prostaglandin A, a prostaglandin J, a derivative of a prostaglandin A or a derivative of a prostaglandin J.

2. A method according to claim 1, wherein the prostaglandin comprises a prostaglandin A or a derivative thereof.

3. A method according to claim 2, wherein the prostaglandin comprises PGA$_1$, PGA$_2$, 16,16-dimethyl-PGA$_1$, 16,16-dimethyl-PGA$_2$, $\Delta^7$-PGA$_1$, $\Delta^7$-PGA$_2$, an alkyl-substituted PGA, a halogen-containing PGA, or a PGA ester.

4. A method according to claim 3, wherein the prostaglandin comprises an alkyl-substituted PGA wherein the alkyl group comprises 1–5 carbon atoms.

5. A method according to claim 2, wherein the prostaglandin comprises an alkyl ester of a PGA having 1–10 carbons in the alkyl group or a benzyl ester of a PGA.

6. A method according to claim 2, wherein the prostaglandin comprises a methyl, ethyl or isopropyl ester of a PGA.

7. A method according to claim 2, wherein the prostaglandin comprises an isopropyl ester of a PGA.

8. A method according to claim 2, wherein the prostaglandin comprises PGA$_2$.

9. A method according to claim 1, wherein the prostaglandin comprises a prostaglandin J or a derivative thereof.

10. A method according to claim 9, wherein the prostaglandin comprises PGJ$_1$, PGJ$_2$, $\Delta^{12}$PGJ$_2$, an alkyl-substituted PGJ, a halogen-containing PGJ, or a PGJ ester.

11. A method according to claim 10, wherein the prostaglandin comprises an alkyl-substituted PGJ wherein the alkyl group comprises 1–5 carbon atoms.

12. A method according to claim 9, wherein the prostaglandin comprises an alkyl ester of a PGJ having 1–10 carbons in the alkyl group or a benzyl ester of a PGJ.

13. A method according to claim 9, wherein the prostaglandin comprises a methyl, ethyl or isopropyl ester of a PGJ.

14. A method according to claim 9, wherein the prostaglandin comprises an isopropyl ester of a PGJ.

15. A method according to claim 9, wherein the prostaglandin comprises PGJ$_2$.

16. A method according to claim 1, wherein the prostaglandin is applied in an amount sufficient to apply from 0.01 to 100 micrograms of prostaglandin.

17. A method according to claim 1, wherein the prostaglandin is applied in an amount sufficient to apply from 1 to 50 micrograms prostaglandin.

18. A method according to claim 1, wherein the prostaglandin is in an aqueous vehicle and the aqueous vehicle further comprises a preservative.

19. A method according to claim 1, wherein the prostaglandin is applied for treatment of secondary cataract.

20. A method according to claim 1, wherein the prostaglandin is applied for prevention of secondary cataract.

\* \* \* \* \*

UNITED STATES PATENT AND TRADEMARK OFFICE
CERTIFICATE OF CORRECTION

PATENT NO. : 5,760,075
DATED : June 2, 1998
INVENTOR(S) : Johan Stjernschantz et al.

It is certified that error appears in the above-identified patent and that said Letters Patent is hereby corrected as shown below:

Claim 3, column 6, line 13, after "ester", insert --, or a derivative of any said compounds--.

Claim 4, column 6, line 16, after "atoms", insert --, or a derivative of any said compounds--.

Claim 5, column 6, line 19, after "PGA", insert --, or a derivative of any of said compounds--.

Claim 6, column 6, line 23, after "PGA", insert --, or a derivative of any of said compounds--.

Claim 7, column 6, line 25, after "PGA", insert --, or a derivative of any of said compounds--.

Claim 8, column 6, line 27, after "$PGA_2$", insert --, or a derivative of $PGA_2$--.

Claim 10, column 6, line 32, after "ester", insert --, or a derivative of any of said compounds--.

UNITED STATES PATENT AND TRADEMARK OFFICE
CERTIFICATE OF CORRECTION

PATENT NO. : 5,760,075
DATED : June 2, 1998
INVENTOR(S) : Johan Stjernschantz et al.

It is certified that error appears in the above-identified patent and that said Letters Patent is hereby corrected as shown below:

Claim 11, column 6, line 35, after "atoms", insert --, or a derivative of any of said compounds--.

Claim 12, column 6, line 39, after "PGJ", insert --, or a derivative of any of said compounds--.

Claim 13, column 6, line 41, after "PGJ", insert --, or a derivative of any of said compounds--.

Claim 14, column 6, line 43, after "PGJ", insert --, or a derivative of any of said compounds--.

Claim 15, column 6, line 45, after "$PGJ_2$", insert --, or a derivative of $PGJ_2$--.

UNITED STATES PATENT AND TRADEMARK OFFICE
CERTIFICATE OF CORRECTION

PATENT NO. : 5,760,075
DATED : June 2, 1998
INVENTOR(S) : Johan Stjernschantz et al.

It is certified that error appears in the above-identified patent and that said Letters Patent is hereby corrected as shown below:

Claim 16, column 6, line 47, after "landin", insert --or prostaglandin derivative--; and
line 48, after "prostaglandin", insert --or prostaglandin derivative, respectively--.

Claim 17, column 6, line 50, after "landin", insert --or prostaglandin derivative--; and
line 51, after "prostaglandin", insert --or prostaglandin derivative, respectively--.

Claim 18, column 6, line 53, after "landin", insert --or prostaglandin derivative--.

Claim 19, column 6, line 56, after "landin", insert --or prostaglandin derivative--.

Claim 20, column 6, line 58, after "landin", insert --or prostaglandin derivative--.

Signed and Sealed this

First Day of September, 1998

*Attest:*

BRUCE LEHMAN

*Attesting Officer*   Commissioner of Patents and Trademarks